United States Patent
Cheetham

(10) Patent No.: US 6,899,537 B2
(45) Date of Patent: May 31, 2005

(54) DENTAL CARTRIDGE

(75) Inventor: Joshua James Cheetham, Prahran (AU)

(73) Assignee: SDI Limited, Victoria (AU)

( * ) Notice: Subject to any disclaimer, the term of this patent is extended or adjusted under 35 U.S.C. 154(b) by 54 days.

(21) Appl. No.: 10/239,997

(22) PCT Filed: Mar. 30, 2001

(86) PCT No.: PCT/AU01/00359

§ 371 (c)(1),
(2), (4) Date: Sep. 27, 2002

(87) PCT Pub. No.: WO01/72235

PCT Pub. Date: Oct. 4, 2001

(65) Prior Publication Data

US 2003/0096212 A1 May 22, 2003

(30) Foreign Application Priority Data

Mar. 31, 2000 (AU) .............................. PQ 6609

(51) Int. Cl.⁷ .............................................. A61C 5/04
(52) U.S. Cl. ....................................................... 433/90
(58) Field of Search ...................... 433/89, 90; 222/326

(56) References Cited

U.S. PATENT DOCUMENTS

| | | | | |
|---|---|---|---|---|
| 1,469,004 A | * | 9/1923 | Gustav | 433/90 |
| 2,573,547 A | * | 10/1951 | Crowell | 433/90 |
| 5,165,890 A | * | 11/1992 | Discko, Jr. | 433/90 |
| 5,286,257 A | * | 2/1994 | Fischer | 604/82 |
| 5,722,830 A | * | 3/1998 | Brandhorst et al. | 433/90 |
| 2003/0186191 A1 | * | 10/2003 | Lawlter et al. | 433/90 |

FOREIGN PATENT DOCUMENTS

| | | |
|---|---|---|
| DE | 27 41 185 | 2/1979 |
| DE | 35 33 367 | 2/1987 |
| FR | 2 642 299 | 8/1990 |
| WO | 81/02250 | 8/1981 |
| WO | 93/16653 | 9/1993 |

OTHER PUBLICATIONS

Derwent Abstract Accession No. 91–214141/29, Class 932, SU 1606116 A (Mukhin I G) Nov. 15, 1990.

English language abstract of FR 2642299.

Derwent English language abstract of DE 27 41 185.

Derwent English language abstract of DE 35 33 367.

* cited by examiner

*Primary Examiner*—Cary E. O'Connor
(74) *Attorney, Agent, or Firm*—William H. Holt

(57) ABSTRACT

A dental cartridge (10) for dispensing a dental cartridge substance (26). The dental cartridge (10) has a dispensing region (18) which is of substantially constant internal diameter. The dispensing region (18) is at least partially curved. A deformable piston (24) is provided and arranged to pass through the curved portion of the dispensing region (18).

14 Claims, 2 Drawing Sheets

DENTAL CARTRIDGE

FIELD OF THE INVENTION

The present invention relates to a dental cartridge.

It is known to require a container in which a dental substance (for instance a cavity filling material) may be stored without contact to light, and from which the substance may be directly dispensed to a required location on or inside a patient's tooth. Various devices have been used for this purposes, including cylindrical tubes with hollow, angular protrusions, torroidal cartridges with co-axial nozzles, and cylindrical cartridges with curved, tapered dispensing nozzles.

Several problems are commonly experienced with such dental containers. Many dental substances are complex mixtures of materials, with particular properties. The effect of shear forces inherent in many of the above designs can be to undesirably change the properties of the filling material. Other materials may not be extrudable through reduced diameter nozzles. A further problem is that dental substances are often wasted due to the impossibility of completely emptying such containers by the application of a conventional plunging mechanism.

The present invention attempts to overcome at least in part some of the aforementioned disadvantages of previous dental substance dispensers.

SUMMARY OF THE PRESENT INVENTION

In accordance with one aspect of the present invention there is provided a dental cartridge for dispensing a dental substance, characterized in that the dental cartridge is hollow and has a dispensing region of substantially constant internal dimension, said dispensing region being curved at least in part, and a piston having a first end, the first end of the piston having an external dimension conforming with the internal dimension of the dispensing region, the piston being arranged so as to be able to pass through the dispensing region including the curved part thereof.

BRIEF DESCRIPTION OF THE DRAWINGS

The present invention will now be described, by way of example, with reference to the accompanying drawings, in which.

DESCRIPTION OF THE INVENTION

Figure 1:
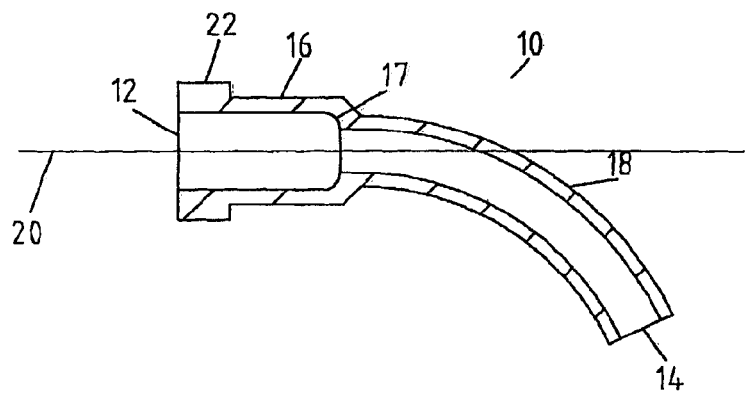
FIG. 1 is a cross sectional view of a dental cartridge in accordance with the present invention.
Figure 2:
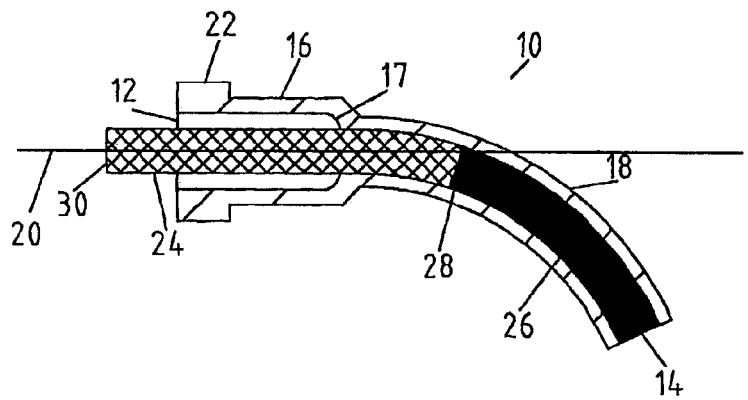
FIG. 2 is a cross sectional view of the dental cartridge of FIG. 1 which has been prepared for use.
Figure 3:
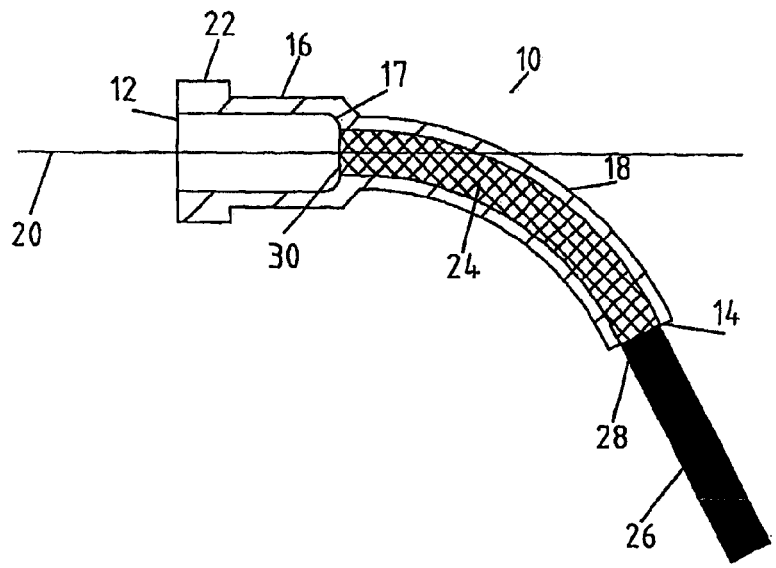
FIG. 3 is a cross sectional view of the dental cartridge of FIG. 1 after use.

Referring to FIGS. 1 to 3 of the accompanying drawings, there is shown a dental cartridge 10 having a first end 12 and a second end 14. The cartridge 10 includes an introducing region 16 of circular cross section and substantially constant internal radius adjacent the first end 12, and a dispensing region 18, also of circular cross section and substantially constant internal radius, adjacent the second end 14. As shown, the internal radius of the dispensing region 18 may be smaller than that of the introducing region 16.

Typically, the cartridge 10 is formed of an opaque plastic material. Further, the internal diameter of the dispensing region 18 is preferably in the range from 1 mm to 6 mm.

The introducing region 16 is straight and extends from the first end 12 of the dental cartridge 10 to an intermediate interface 17. The introducing region 16 is generally cylindrical in shape with a longitudinal axis 20. An outwardly extending flanged portion 22 is located adjacent the first end 12 of the introducing region 16. The flanged portion 22 is circular and has an external radius greater than that of the remainder of the introducing region 16. The flanged portion 22 allows the dental cartridge 10 to be attached, in use, to a dispensing device (not shown).

The introducing region 16 is in communication with the exterior of the dental cartridge at the first end 12, and is in communication with the dispensing region 18 at the intermediate interface 17.

The dispensing region 18 extends from the intermediate interface 17 to the second end 14 of the dental cartridge 10. The dispensing region 18 is curved in such a way that at the intermediate interface 17 the longitudinal axis of the dispensing region 18 is co-axial with the longitudinal axis 20 of the introducing region 16, whereas at the second end 14 the longitudinal axis of the dispensing region 18 is orientated at an angle with respect to axis 20.

The internal radius of the dispensing region 18 is substantially constant to provide, in use, a fluid flow path substantially free of shearing forces. The external radius of the dispensing region 18 may taper from a radius equal to the external radius of the introducing region 16 at the intermediate interface 17 to a smaller radius at the second end 14. In this case, the wall thickness of the introducing region 16 is thus smaller at the second end 14 than at the interface 17.

FIG. 2 shows the present invention in a state immediately prior to use. At least a portion of the dispensing region 18 adjacent the second end 14 contains a quantity of a dental substance 26. A deformable piston 24 is introduced into the dental cartridge 10 through the introducing region 16. The deformable piston 24 is generally cylindrical in shape, with an external radius approximately equal to the internal radius of the dispensing region 18. The deformable piston 24 has a first end 28 which abuts the dental substance 26 and a second or free end 30 initially located outside of the dental cartridge 10. It will be appreciated that the deformable piston 24 may be of another configuration, provided the first end 28 is substantially complementary in shape to the interior of the dispensing region 18.

In use, at least a portion of the dispensing region 18 is loaded with a quantity of a dental substance 26, and a deformable piston 24 is introduced through the introducing region 16. Application of a pushing force on the free end 30 of the deformable piston 24 causes the deformable piston 24 to move through the dental cartridge 10, thus dispensing the dental substance 26 from the second end 14 of the dispensing region 18 on or into the desired location. The deformable or flexible nature of the piston 24 enables the piston 24 to travel through the curved portion of the dispensing region 18 whilst conforming closely with the internal walls of the dispensing region 18.

FIG. 3 shows the dental cartridge 10 of FIG. 2 after use, where the deformable piston 24 has completely displaced the dental substance 26 in the dispensing region 18.

Figure 4:
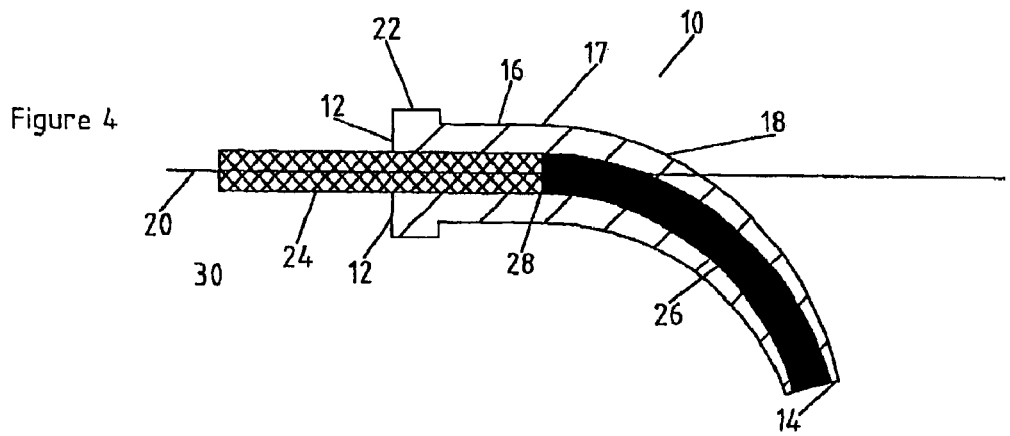
FIG. 4 is a cross sectional view of a second embodiment of the dental cartridge of the present invention which has been prepared for use.

A second embodiment of the present invention is shown in FIG. 4, where the introducing region 16 and the dispensing region 18 have the same internal radius. In this embodiment the intermediate interface 17 is not distinguishable from the introducing region 16 and the dispensing region 18.

Figure 5:
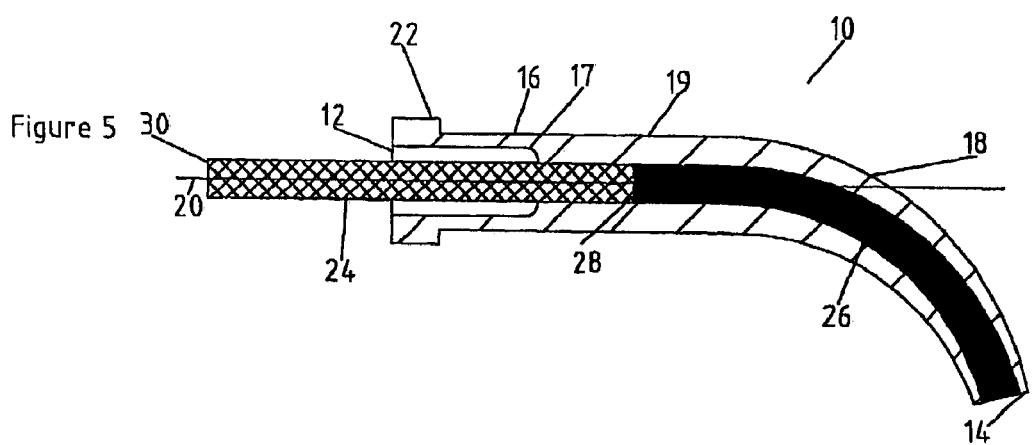
FIG. 5 is a cross sectional view of a third embodiment of the dental cartridge of the present invention which has been prepared for use.

A third embodiment of the present invention is shown in FIG. 5. In this embodiment the dispensing region 18 includes a straight portion 19 adjacent the intermediate interface 17, in which the straight portion 19 has a longitudinal axis which is co-axial with the longitudinal axis 20 of the introducing region 16.

Figure 6:
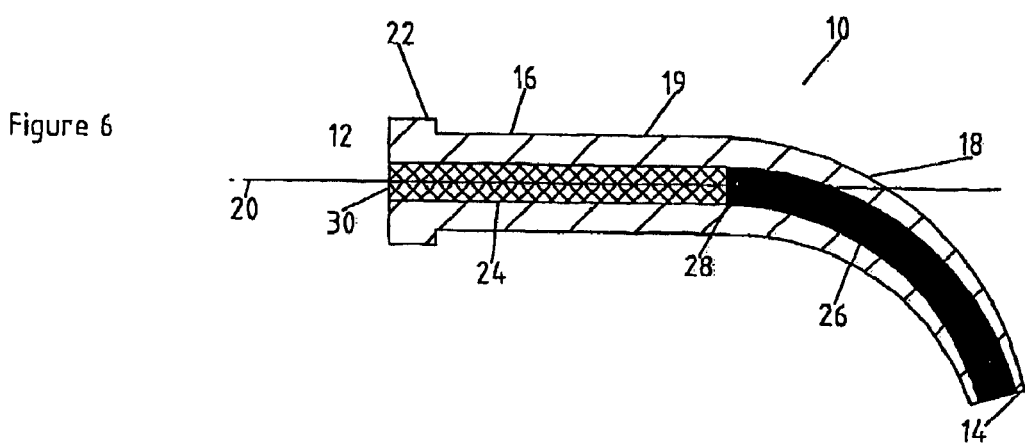
FIG. 6 is a cross sectional view of a fourth embodiment of the dental cartridge of the present invention which has been prepared for use.

A fourth embodiment is shown in FIG. 6. This embodiment also includes a straight portion 19 which has an, internal radius equal to that of both the introducing region 16 and the dispensing region 18.

It is envisaged that the piston 24 could be made in various lengths and shapes so that in some embodiments the piston 24 could be relatively short whilst in other embodiments the piston 24 could be relatively long.

Further, it is envisaged that when the cartridge 10 contains a dental substance 26 the second end 14 could be closed off by an opaque cap to prevent ingress of radiation.

Modifications and variations as would be apparent to a skilled addressee are deemed to be within the scope of the present invention. For instance, the flanged portion 22 may be replaced with another means for attaching the dental cartridge 10 to a dispensing device, such as a Luer lock flange, a flange with a threaded portion, or a circumscribing groove on the external surface of the introducing region 16.

What is claimed is:

1. A dental cartridge for dispensing a dental substance, wherein the dental cartridge is hollow and has a dispensing region of substantially constant internal dimension, said dispensing region having a curved part, the dispensing region containing a quantity of a dental substance within the curved part, the dental cartridge including a piston comprised of a unitary deformable member, the piston having a first end, the first end of the piston having an external dimension conforming with the internal dimension of the dispensing region, the piston being arranged so as to be able to pass through the dispensing region including the curved part thereof for displacing and dispensing the dental substance from the dispensing region including the curved part thereof substantially free of shearing forces.

2. A dental cartridge according to claim 1, wherein the piston is in the form of a cylinder.

3. A dental cartridge according to claim 1, wherein the dental cartridge has a first end and second end, the first end being remote from the dispensing region and the second end being adjacent an outer end of the dispensing region, and wherein the dental cartridge has an introducing region of substantially constant internal dimension extending from the first end, the piston being receivable within the introducing region.

4. A dental cartridge according to claim 3, wherein the internal dimension of the introducing region is larger than the internal dimension of the dispensing region.

5. A dental cartridge according to claim 3, wherein the introducing portion is substantially circular in cross section.

6. A dental cartridge according to claim 3, wherein the dental cartridge includes a portion adjacent the first end for attachment to a dispensing device.

7. A dental cartridge according to claim 6, wherein the portion for attachment to a dispensing device is in the form of an outwardly extending flange.

8. A dental cartridge according to claim 6, wherein the portion for attachment to a dispensing device is at least partially threaded.

9. A dental cartridge according to claim 6, wherein the portion for attachment to a dispensing device includes a Luer lock.

10. A dental cartridge according to claim 6, wherein the portion for attachment to a dispensing device includes a circumscribing groove.

11. A dental cartridge according to claim 1, wherein the dispensing region has an external dimension which tapers in size and is smallest at a second end of the dental cartridge.

12. A dental cartridge according to claim 1, wherein the dispensing region includes a substantially straight portion.

13. A dental cartridge according to claim 1, wherein the dispensing region is substantially circular in cross section.

14. A dental cartridge according to claim 13, wherein the dispensing region has an internal diameter in the range 1 mm to 6 mm.

* * * * *